United States Patent
Hirano et al.

(10) Patent No.: US 10,401,355 B2
(45) Date of Patent: Sep. 3, 2019

(54) TEST REAGENT, TEST REAGENT KIT, AND SPECIMEN MEASURING SYSTEM

(71) Applicant: Toshiba Medical Systems Corporation, Otawara-shi (JP)

(72) Inventors: Asuka Hirano, Nasushiobara (JP); Shoichi Kanayama, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 281 days.

(21) Appl. No.: 15/209,954

(22) Filed: Jul. 14, 2016

(65) Prior Publication Data
US 2017/0023563 A1    Jan. 26, 2017

(30) Foreign Application Priority Data
Jul. 23, 2015 (JP) .................................. 2015-145628

(51) Int. Cl.
| | | |
|---|---|---|
| *B01L 3/00* | (2006.01) | |
| *G01N 33/543* | (2006.01) | |
| *G01N 21/552* | (2014.01) | |
| *G01N 21/77* | (2006.01) | |
| *G01N 21/82* | (2006.01) | |
| *G01N 21/76* | (2006.01) | |

(52) U.S. Cl.
CPC ..... *G01N 33/54373* (2013.01); *G01N 21/552* (2013.01); *G01N 21/77* (2013.01); *G01N 21/82* (2013.01); *G01N 33/54326* (2013.01); *B01L 3/5023* (2013.01); *G01N 21/76* (2013.01); *G01N 2021/7786* (2013.01); *G01N 2021/825* (2013.01)

(58) Field of Classification Search
CPC ....... G01N 33/54373; G01N 33/54326; G01N 21/77; G01N 21/82; G01N 21/552; G01N 2021/825; G01N 2021/7786; G01N 21/76; B01L 3/5023
See application file for complete search history.

(56) References Cited

U.S. PATENT DOCUMENTS

| | | | | |
|---|---|---|---|---|
| 4,859,583 | A * | 8/1989 | Heller | .............. G01N 33/54366 435/7.7 |
| 4,923,680 | A * | 5/1990 | Nelson | .................... B01D 61/18 210/506 |
| 5,756,049 | A * | 5/1998 | Brayton | .............. B01L 3/50825 422/430 |
| 2005/0287682 | A1* | 12/2005 | Lizzi | ...................... B01L 3/502 436/526 |

FOREIGN PATENT DOCUMENTS

| | | |
|---|---|---|
| JP | 2-48505 | 2/1990 |
| JP | 2-296152 | 12/1990 |
| JP | 5-187976 A | 7/1993 |

(Continued)

OTHER PUBLICATIONS

Japanese Office Action dated Oct. 23, 2018 in Patent Application No. 2015-145628, 3 pages.

*Primary Examiner* — Rebecca L Martinez
(74) *Attorney, Agent, or Firm* — Oblon, McClelland, Maier & Neustadt, L.L.P.

(57) ABSTRACT

A test reagent includes a reactant and a sheet-shaped member. The reactant is in a dry state and specifically reacts with a test substance. The sheet-shaped member holds the reactant and disperses in a solvent solution in which the reactant dissolves.

13 Claims, 8 Drawing Sheets

(56) References Cited

FOREIGN PATENT DOCUMENTS

| JP | 6-16043 | 3/1994 |
| JP | 2002-504985 A | 2/2002 |
| JP | 2008-504560 A | 2/2008 |
| JP | 2013-217882 | 10/2013 |
| JP | 2014-98715 | 5/2014 |

* cited by examiner

TEST REAGENT, TEST REAGENT KIT, AND SPECIMEN MEASURING SYSTEM

CROSS-REFERENCE TO RELATED APPLICATIONS

This application is based upon and claims the benefit of priority from the prior Japanese Patent Application No. 2015-145628, filed Jul. 23, 2015 the entire contents of which are incorporated herein by reference.

FIELD

Embodiments described herein relate generally to a test reagent, a test reagent kit, and a specimen measuring system.

BACKGROUND

There is a dry type reagent to be used to measure a test substance in a sample. For example, in a test kit using immunochromatography, a reagent component that specifically reacts with a test substance is dried and immobilized on a membrane. When a sample is dropped to the portion of the reagent component on the membrane, the reagent component is eluted into the sample. Then, the measurement solution moving on the membrane is irradiated with light, thereby measuring the test substance in the sample.

There also exists a liquid type reagent. A reagent container storing a liquid type reagent containing a reagent component in an amount corresponding to a plurality of measurements is set in a specimen measuring apparatus. The reagent in the set reagent container is dispensed into a reaction vessel in which a sample is dispensed. The solution mixture of the sample and the reagent in the reaction vessel is irradiated with light, thereby measuring the test substance.

However, in the dry type reagent, the reagent component is not evenly diffused when it is eluted by the sample. It is therefore pointed out that a nonspecific reaction and a decrease in sensitivity occur. Additionally, in the liquid type reagent, the reagent component separates in the reagent container when left standing for a long time. It is therefore necessary to stir and diffuse the reagent component before dispensing into the reaction vessel.

DETAILED DESCRIPTION

In general, according to one embodiment, a test reagent includes a reactant and a sheet-shaped member. The reactant is in a dry state and specifically reacts with a test substance. The sheet-shaped member holds the reactant and disperses in a solvent solution in which the reactant dissolves.

The embodiments will now be described with reference to the accompanying drawings.

First Embodiment

Figure 1:
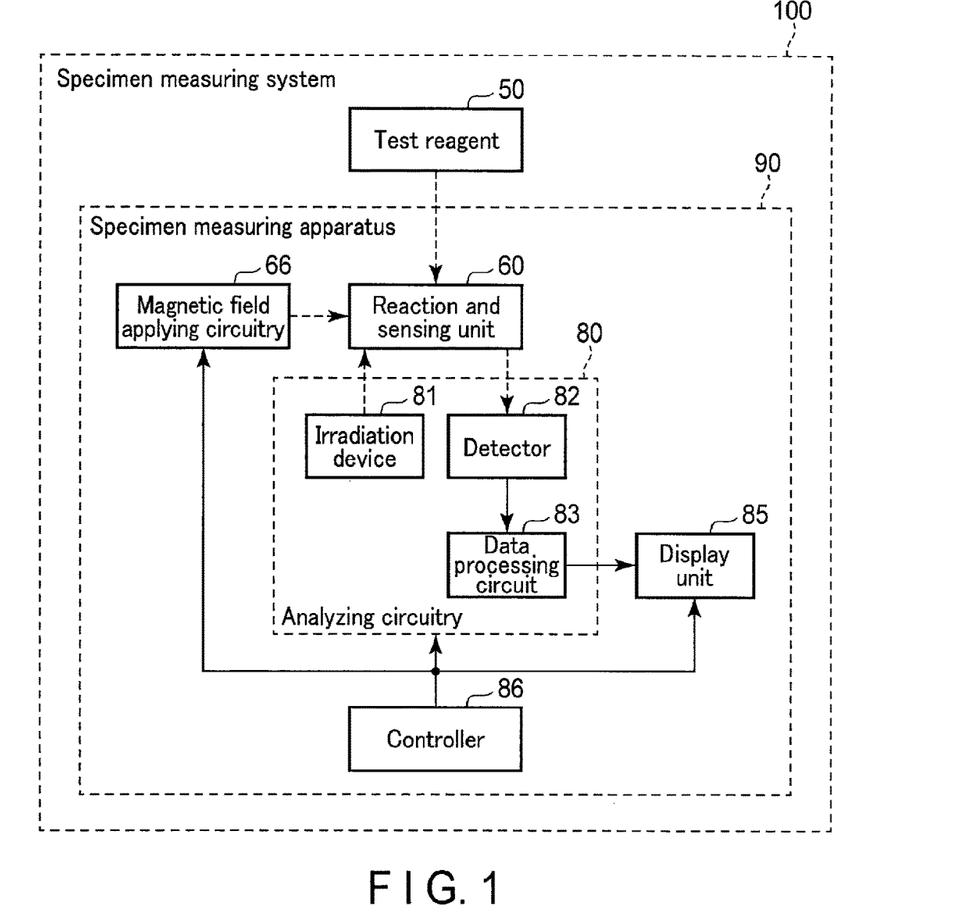
FIG. 1 is a block diagram showing the arrangement of a specimen measuring system according to the first embodiment.

FIG. 1 is a block diagram showing a specimen measuring system according to the first embodiment. A specimen measuring system 100 includes a test reagent 50 that specifically reacts with a test substance A contained in a sample collected from an object, and a specimen measuring apparatus 90 that measures the test substance A in the sample using the test reagent 50.

The test reagent 50 will be described first.

Figure 2:
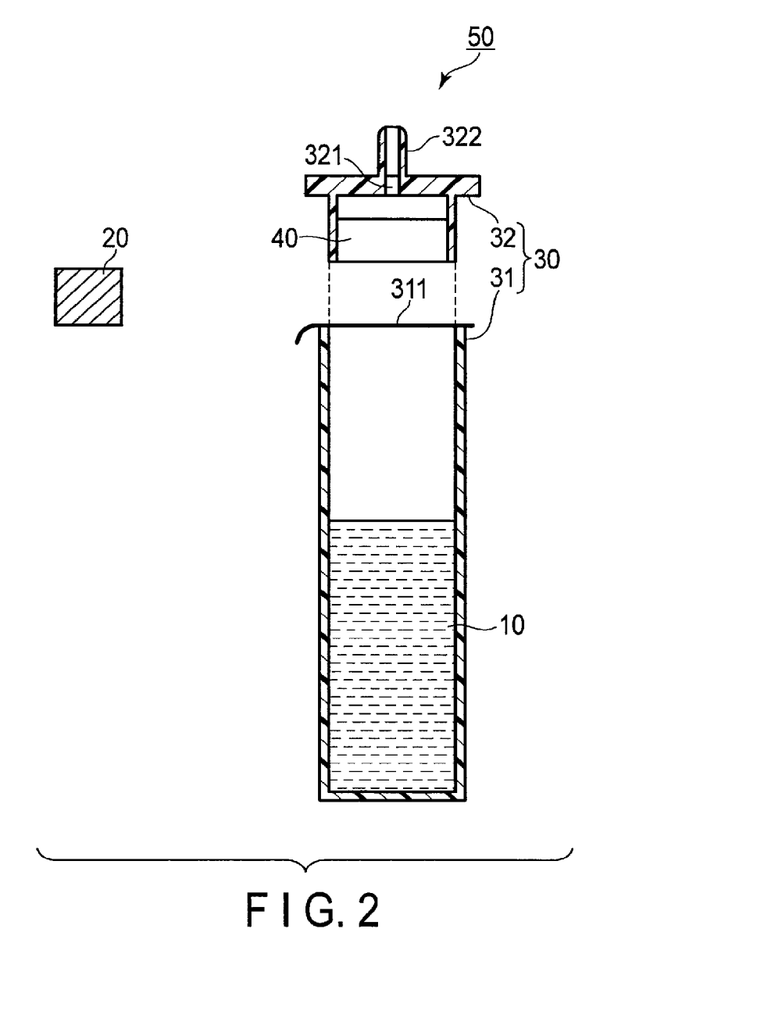
FIG. 2 is a view showing an example of the arrangement of a test reagent according to the first embodiment.

FIG. 2 is a view showing an example of the arrangement of the test reagent 50 as a test reagent kit. The test reagent 50 includes, for example, an aqueous solution 10 such as a buffer solution, and a dry reagent 20 that specifically reacts with the test substance A in the aqueous solution 10. The test reagent 50 also includes a container 30 storing the aqueous solution 10, and a filter 40 configured to filter and separate the dry reagent 20 put in the aqueous solution 10 in the container 30.

Figure 3:
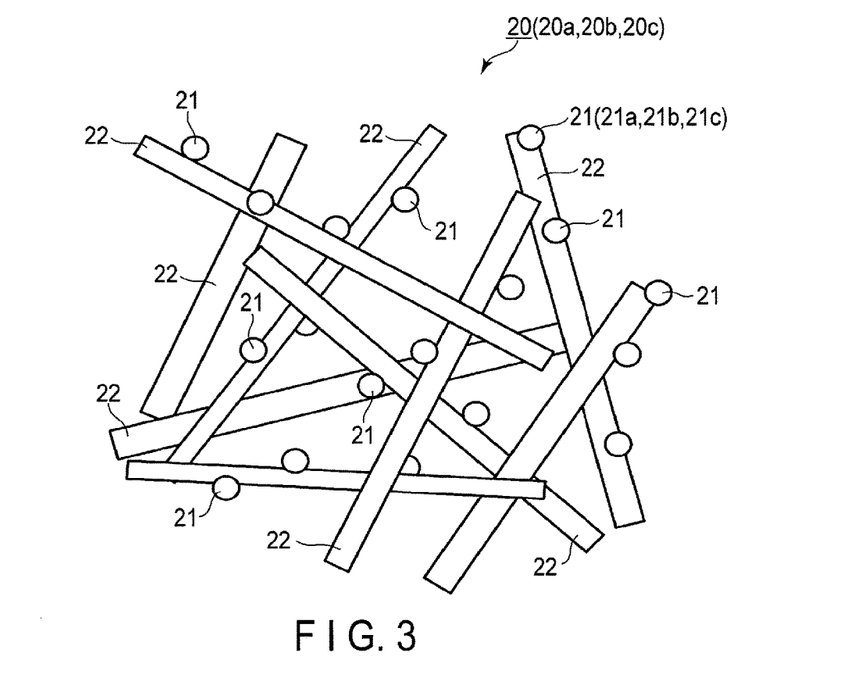
FIG. 3 is a schematic view showing the structure of a dry reagent according to the first embodiment.

FIG. 3 is a schematic view showing the structure of the dry reagent 20. The dry reagent 20 has, for example, a rectangular sheet shape. The dry reagent 20 is formed from a reagent component 21 and a holding membrane 22. The reagent component 21 is in a dry state and specifically reacts with the test substance A in the aqueous solution 10. The reagent component 21 in the dry state is dispersed and held by the holding membrane 22. Although not illustrated, the dry reagent 20 is hermetically preserved in a package in the dry state.

Note that the dry reagent 20 may be arranged on the filter 40, and a lid 32, the dry reagent 20, and the filter 40 that are in a dry state may hermetically be preserved in one package.

As described above, the reagent component 21 in the dry state is held by the holding membrane 22, and the dry reagent 20 is preserved in the dry state. This makes it possible to prevent the reagent component 21 from deteriorating and preserve it for a long time.

The reagent component 21 is formed from a reactant that specifically reacts with the test substance A in the aqueous solution 10 and fine particles on which the reactant is immobilized. The reactant is held by the holding membrane 22 by, for example, holding the fine particles by the holding membrane 22. The holding membrane 22 has a sheet shape and is made of a fibrous substance containing, for example, cellulose or a water soluble resin such as a water soluble polyester resin which easily disperses in the aqueous solution 10 and is not concerned in the reaction between the test substance A and the reagent component 21. The holding membrane 22 holds the reagent component 21 whose dry weight is a predetermined weight.

As described above, when the reagent component 21 is dispersed and held by the holding membrane 22, the holding membrane 22 is dispersed in the aqueous solution 10, and the reagent component 21 is dissolved from the dispersed holding membrane 22. It is therefore possible to prevent the reagent component 21 from remaining undissolved and coagulating and easily diffuse it in the aqueous solution 10.

The container 30 shown in FIG. 2 includes a storage vessel 31 having an opening portion at one end in the longitudinal direction and storing a predetermined amount of aqueous solution 10. The container 30 also includes the lid 32 having, on one end side, an insertion portion that can be inserted and fitted into the opening portion of the storage vessel 31. The storage vessel 31 is made of, for example, low density polyethylene that is soft and transparent. The opening portion is sealed by a removable sealing member 311 so as to prevent the aqueous solution 10 from leaking to the outside. The lid 32 has, on the other end side, a nozzle 322 with a through hole 321 communicating with the inside of the insertion portion.

The filter 40 is arranged, for example, inside the insertion portion of the lid 32 of the container 30. The filter 40 is provided to separate the holding membrane 22 dispersed in the aqueous solution 10, which is generated by adding the dry reagent 20 to the aqueous solution 10 in the storage vessel 31, and a measurement solution containing the sample and the aqueous solution 10 in which the reagent component 21 other than the holding membrane 22 is diffused. The measurement solution separated by the filter 40 in the container 30 flows through the through hole 321 and the nozzle 322 and exits to the outside.

An example of the steps in the manufacture of the dry reagent 20 will be described next.

First, a liquid reagent in which the reagent component 21 whose dry weight is n (n is a positive number larger than 1.0) times of a predetermined weight is dissolved is prepared. In addition, a sheet-shaped member made of the material of the holding membrane 22 and having a surface area n times larger than the surface area of the holding membrane 22 is prepared. A container with a flat bottom surface is prepared as well. After the container is arranged such that the surface of the prepared member becomes level, the liquid reagent is applied or sprayed so as to form an even layer on the surface of the member. Water in the applied or sprayed liquid reagent is evaporated to dry the reagent. After that, the member is cut into the size of a predetermined surface area such that the dry weight of the reagent component 21 becomes the predetermined weight, thereby producing the dry reagent 20.

With this manufacturing process, the dry reagent 20 in which a predetermined weight of reagent component 21 in the dry state is dispersed and held by the holding membrane 22 can be produced.

The specimen measuring apparatus 90 shown in FIG. 1 will be described next. The specimen measuring apparatus 90 measures the measurement solution separated by the filter 40 of the test reagent 50, and includes a reaction and sensing unit 60 that stores the measurement solution, and a magnetic field applying circuitry 66 that applies magnetic fields to the reaction and sensing unit 60. The specimen measuring apparatus 90 also includes analyzing circuitry 80 that analyzes a reaction state of the measurement solution stored in the reaction and sensing unit 60, and display unit 85 that visualizes the analyzing result based on output data from the analyzing circuitry 80. The specimen measuring apparatus 90 also includes a controller 86 that is a processor functioning as the main unit of the specimen measuring apparatus 90. The controller 86 executes a control program stored in storage circuitry, thereby implementing a function corresponding to the program.

Figure 4:
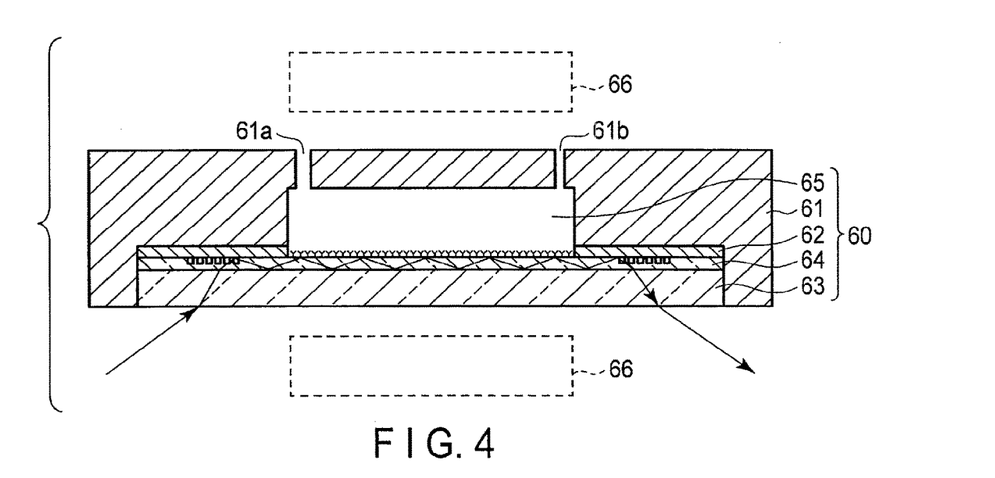
FIG. 4 is a sectional view showing the arrangement of a reaction and sensing unit according to the first embodiment.

FIG. 4 is a sectional view showing the arrangement of the reaction and sensing unit 60. The reaction and sensing unit 60 includes a cartridge frame 61, a plate-shaped shield membrane 62, a plate-shaped transparent substrate 63, and a plate-shaped optical waveguide 64. The reaction and sensing unit 60 also includes a reaction chamber 65 that is formed by the cartridge frame 61, the shield membrane 62, and the optical waveguide 64, and stores the measurement solution.

A first concave portion is formed in the lower surface of the cartridge frame 61. A second concave portion that forms the upper and side surfaces of the reaction chamber 65 is formed in part of the upper surface of the first concave portion. In the first concave portion, the shield membrane 62, the optical waveguide 64, and the transparent substrate 63 are arranged in this order from above. A hole 61a is formed near one end of the upper surface of the second concave portion so as to extend upward through the cartridge frame 61, and a hole 61b is formed near the other end so as to extend upward through the cartridge frame 61.

The shield membrane 62 has an opening at the position of the second concave portion of the cartridge frame 61. The shield membrane 62 is arranged with the upper surface in contact with the upper surface of the first concave portion of the cartridge frame 61 and the lower surface in contact with the upper surface of the optical waveguide 64. The transparent substrate 63 is made of a material that passes light emitted by the analyzing circuitry 80. The transparent substrate 63 is arranged with the upper surface in contact with the lower surface of the optical waveguide 64.

The optical waveguide 64 is made of a material that passes light. The optical waveguide 64 serves as an optical path of light that enters the optical waveguide 64 from the transparent substrate 63 and exits from the optical waveguide 64 to the transparent substrate 63. Namely, the optical waveguide 64 has a function similar to that of the core (core material) of the optical fiber. Each of the shield membrane 62 and the transparent substrate 63 is made of a material having a different refractive index from that of the optical waveguide 64 and functions as a clad that totally reflects light by the boundary surface with respect to the optical waveguide 64 and confines light in the optical waveguide 64. In addition, the shield membrane 62 and the transparent substrate 63 physically protect the optical waveguide 64.

The upper surface of the reaction chamber 65 is formed by the upper surface of the second concave portion of the cartridge frame 61, the side surfaces are formed by the side surfaces of the second concave portion of the cartridge frame 61 and the opening portion surface of the shield membrane 62, and the lower surface is formed by the upper surface of the optical waveguide 64. A substance that specifically reacts with the test substance A is immobilized on the lower surface. The surface of the optical waveguide 64 on which the test substance A is immobilized totally reflects light at the boundary surface (surface inside the optical waveguide 64), and confines light in the optical waveguide 64.

The analyzing circuitry 80 shown in FIG. 1 includes an irradiation device 81 that emits light with a predetermined wave length, for example, a laser or an LED to the transparent substrate 63 from below of the reaction and sensing unit 60 by a predetermined incident angle. Light that has entered the transparent substrate 63 enters the optical waveguide 64, and travels and propagates within the optical waveguide 64 while being totally reflected by the boundary surface of the optical waveguide 64.

The analyzing circuitry 80 also includes a detector 82 that detects the light propagated through the optical waveguide 64 in the reaction and sensing unit 60 and exited from the transparent substrate 63. The analyzing circuitry 80 also includes a processor functioning as a data processing circuit 83 that calculates the amount of the test substance A contained in the sample based on the change of a physical value in relation to the light, for example, change of the intensity of the light, detected by the detector 82.

An example of the operation of the specimen measuring system 100 will be described below with reference to FIGS. 1 to 7. In the following explanation, the reactant of the reagent component 21 contained in the dry reagent 20 that forms the test reagent 50 is, for example, a first antibody that combines with the test substance A serving as an antigen, and the fine particles of the reagent component 21 are magnetic particles. The substance immobilized on the lower surface of the reaction chamber 65 of the reaction and sensing unit 60 of the specimen measuring apparatus 90 is a second antibody that combines with the test substance A serving as an antigen. The dry weight of the reagent component 21 held by the holding membrane 22 is, for example, 30 μg. The container 30 stores 120 μL of the aqueous solution 10.

Figure 5A:
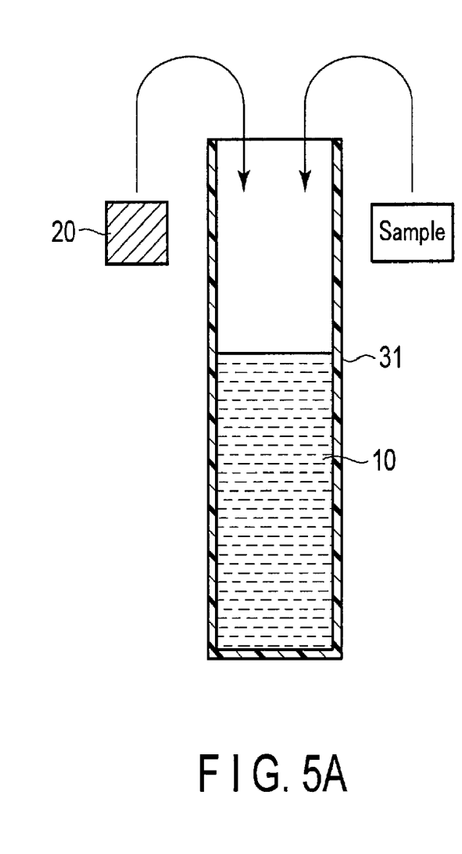
FIG. 5A is a view showing an example of the first step of a procedure of preparing a test reagent and a sample according to the first embodiment.
Figure 5B:
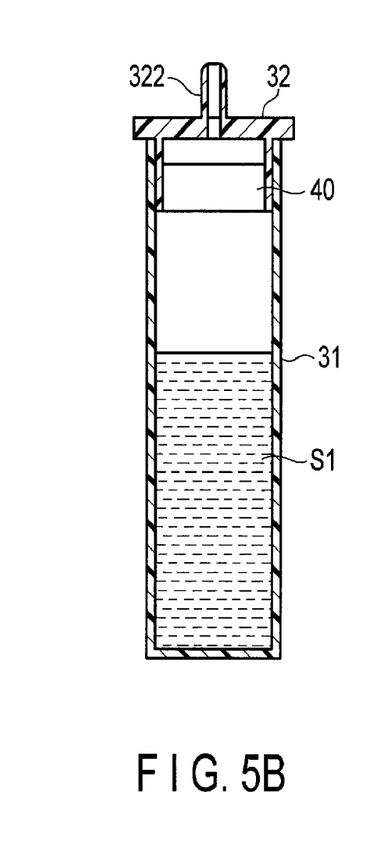
FIG. 5B is a view showing an example of the second step of the procedure of preparing a test reagent and a sample according to the first embodiment.

First, the operator removes the sealing member 311 from the storage vessel 31 of the test reagent 50. Next, as shown in FIG. 5A, the operator puts the dry reagent 20 into the aqueous solution 10 in the storage vessel 31. Then, the holding membrane 22 disperses in the aqueous solution 10, and the reagent component 21 diffuses in the aqueous solution 10. After the dry reagent 20 is put, the operator further puts a sample collected from an object. After putting the dry reagent 20 and the sample, the operator inserts and fits the insertion portion of the lid 32 into the opening portion of the storage vessel 31 and performs, for example, inversion mixing. The holding membrane 22 then disperses in the aqueous solution 10, and a solution mixture S1 in which the reagent component 21 and the sample are diffused is obtained, as shown in FIG. 5B.

As described above, the reagent component 21 is dispersed and held by the holding membrane 22. With the simple operation of only putting the dry reagent 20 into the storage vessel 31, the holding membrane 22 disperses in the aqueous solution 10, and the reagent component 21 is dissolved from the dispersed holding membrane 22. It is therefore possible to prevent the reagent component 21 from remaining undissolved and coagulating and easily diffuse it in the aqueous solution 10. In addition, when the transparent storage vessel 31 is used, the operator can visually confirm the states of the holding membrane 22 and the reagent component 21 in the aqueous solution 10.

Figure 6A:
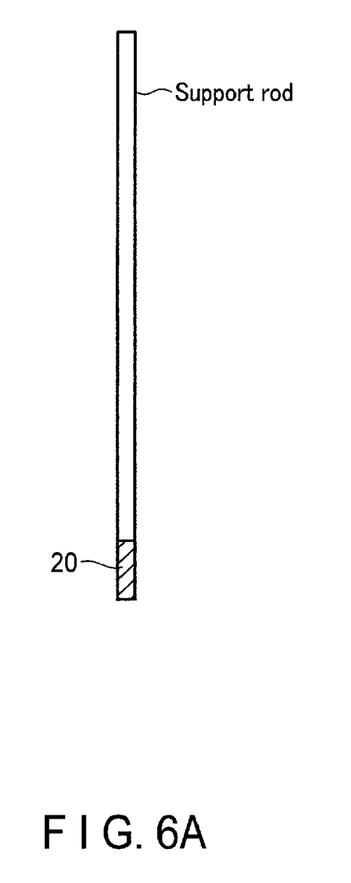
FIG. 6A is a view showing an example of a support rod with a test reagent fixed at the lower end according to the first embodiment.
Figure 6B:
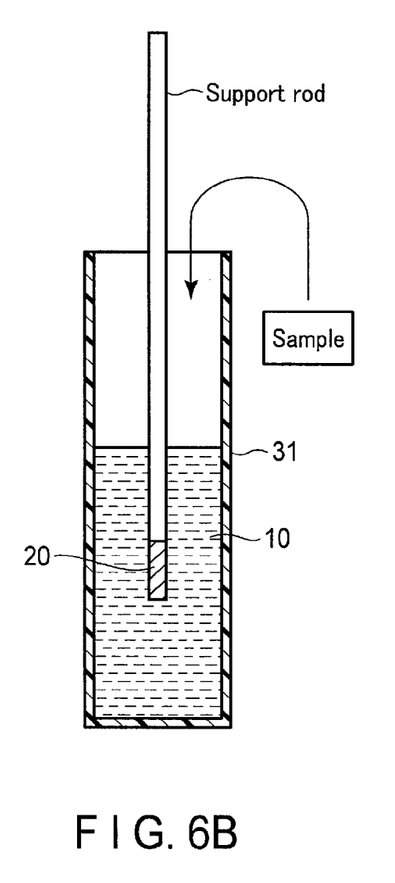
FIG. 6B is a view showing another example of the procedure of preparing a test reagent and a sample according to the first embodiment.

Note that the procedure of preparing the test reagent and the sample is not limited to that described above. The operator may roll up the dry reagent 20 and deform it to, for example, a tubular shape such that the surface on which the reagent component 21 of the dry reagent 20 is held faces outward. As shown in FIG. 6A, the operator may fix one side of the dry reagent 20 as the upper end of the tubular shape to the lower end of a support rod. As shown in FIG. 6B, the operator may stir and mix the dry reagent 20 and the sample put into the aqueous solution 10 in the storage vessel 31 using the support rod. The operator may then insert and fit one end of the lid 32 into the opening portion of the storage vessel 31.

Figure 5C:
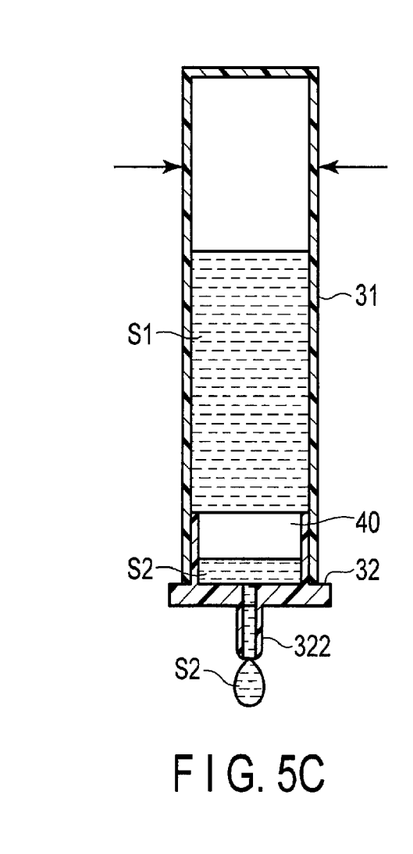
FIG. 5C is a view showing an example of the third step of the procedure of preparing a test reagent and a sample according to the first embodiment.

Next, the test reagent 50 is turned to direct the lid 32 downward, and the nozzle 322 is inserted into the hole 61a of the cartridge frame 61 of the reaction and sensing unit 60 in the specimen measuring apparatus 90. As shown in FIG. 5C, the storage vessel 31 of the container 30 is nipped and pressed in the directions of arrows. Upon this pressing, the holding membrane 22 is removed from the solution mixture S1 by the filter 40, and a measurement solution S2 without the holding membrane 22 is dropped from the lower end of the nozzle 322.

As described above, when the soft storage vessel 31 is used, the operator can separate the holding membrane 22 unnecessary for measurement by the specimen measuring apparatus 90 with the simple operation of nipping and pressing the storage vessel 31.

Figure 7:
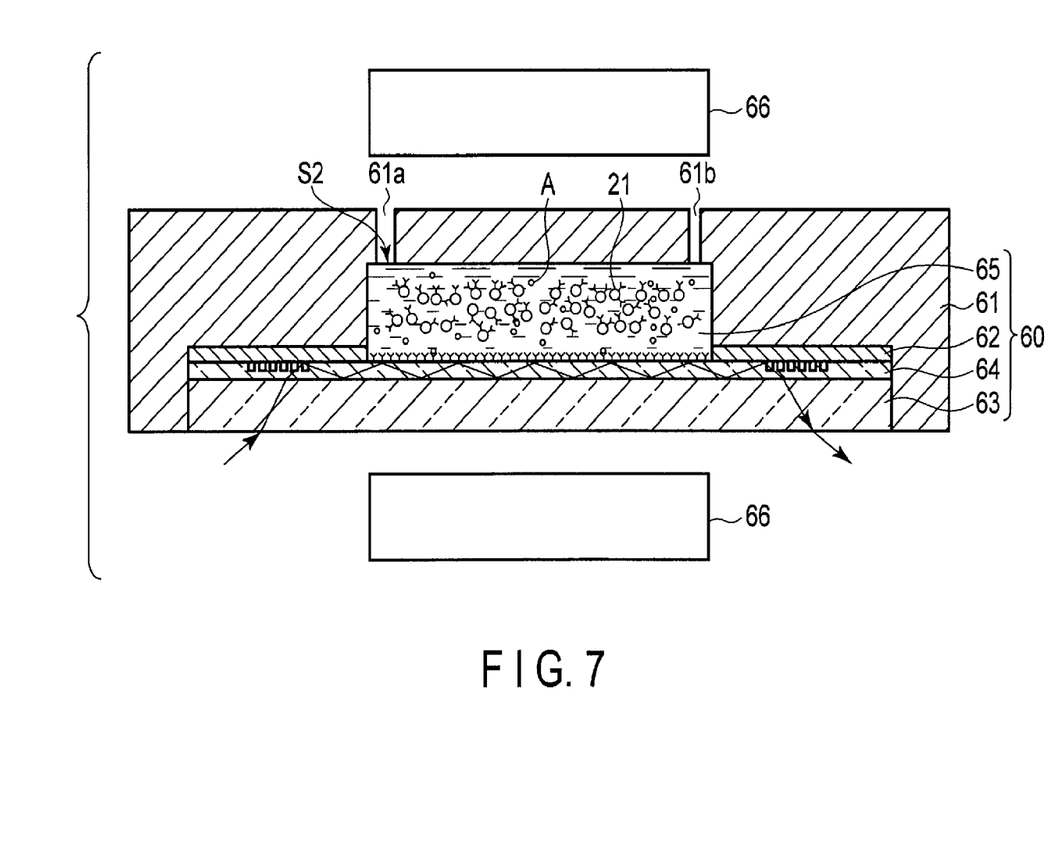
FIG. 7 is a view showing a measurement solution that fills a reaction chamber according to the first embodiment.

The measurement solution S2 dropped from the nozzle 322 flows into the reaction chamber 65 of the reaction and sensing unit 60, and air in the reaction chamber 65 exits from the hole 61b of the cartridge frame 61. Then, the reaction chamber 65 is filled with the measurement solution S2, as shown in FIG. 7. Next, light that is emitted by the irradiation device 81 and exits through the transparent substrate 63 of the reaction and sensing unit 60 enters one end side of the optical waveguide 64. The light that has entered is deflected and then propagated through the optical waveguide 64 toward the other end. The light is propagated through the region of the optical waveguide 64 under the reaction chamber 65 and exits from the other end side of the optical waveguide 64 after deflected to an angle that enables exit from the optical waveguide 64. The detector 82 detects the light that has exited from the optical waveguide 64 and passed through the transparent substrate 63.

The magnetic field applying circuitry 66 applies a downward magnetic field to the reaction chamber 65 and then applies an upward magnetic field. The reagent component 21 in the measurement solution S2 in the reaction chamber 65 combines with the first antibody immobilized on the magnetic particles, thereby trapping the test substance A. When the downward magnetic field is applied, the test substance A trapped by the reagent component 21 combines with the second antibody immobilized on the lower surface of the reaction chamber 65. Then, when the upward magnetic field is applied, only the reagent component 21 that does not trap the test substance A by the second antibody moves upward.

When the test substance A trapped by the reagent component 21 combines with the second antibody immobilized on the lower surface of the reaction chamber 65, the intensity of the light propagated through the optical waveguide 64 lowers due to scattering and absorption in the region under the reaction chamber 65. The intensity of the light that exits from the optical waveguide 64 changes depending on the amount of the test substance A combined with the second antibody immobilized on the lower surface of the reaction chamber 65. When the upward magnetic field is being applied, the analyzing circuitry 80 calculates the amount of the test substance A in the measurement solution S2 based on the intensity of the light that exits from the optical waveguide 64. The display unit 85 displays the amount of the test substance A calculated by the analyzing circuitry 80.

According to the above-described first embodiment, the reagent component 21 in the dry state is held by the holding membrane 22, and the dry reagent 20 is preserved in the dry state. This makes it possible to prevent the reagent component 21 from deteriorating and preserve it for a long time. In addition, the reagent component 21 is dispersed and held by the holding membrane 22. With the simple operation of only putting the dry reagent 20 into the storage vessel 31, the holding membrane 22 disperses in the aqueous solution 10, and the reagent component 21 can easily be diffused in the aqueous solution 10. This enables to easily conduct the test of the test substance A in a short time.

Second Embodiment

Figure 8:
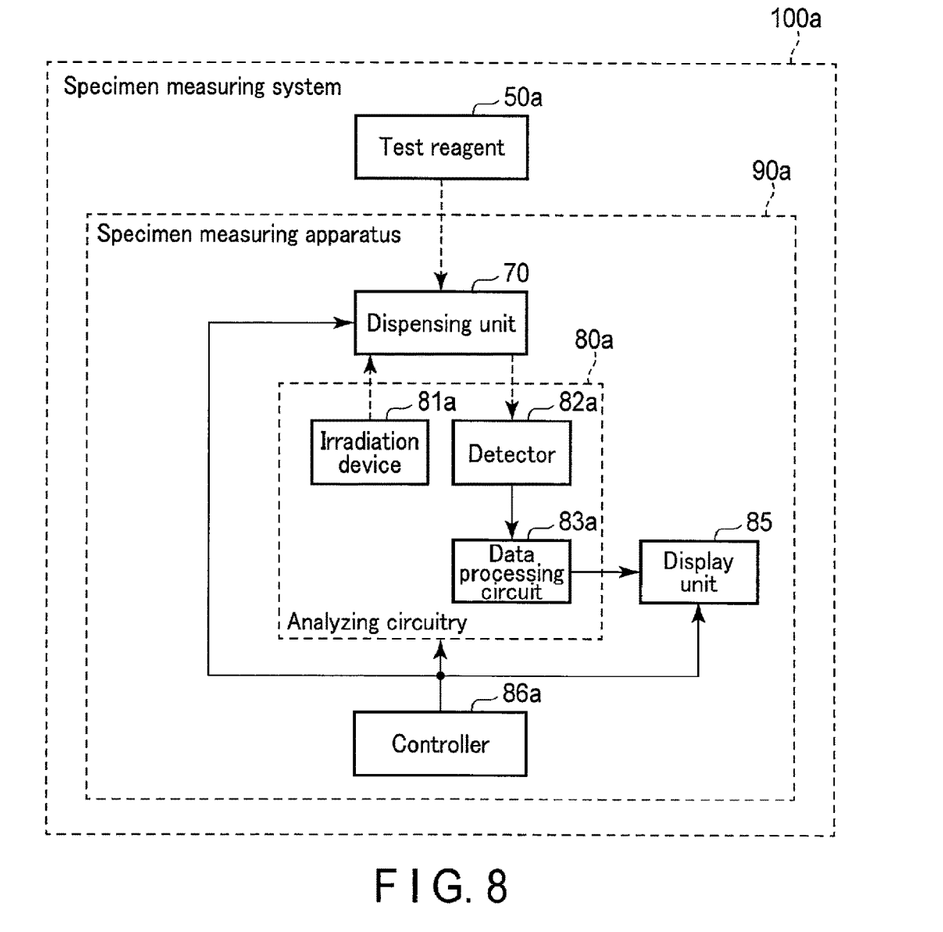
FIG. 8 is a block diagram showing the arrangement of a specimen measuring system according to the second embodiment.

FIG. 8 is a block diagram showing a specimen measuring system according to the second embodiment. A specimen measuring system 100a includes a test reagent 50a that specifically reacts with a test substance B contained in a sample collected from an object, and a specimen measuring apparatus 90a that measures the test substance B in the sample using the test reagent 50a.

The test reagent 50a will be described first.

Figure 9:
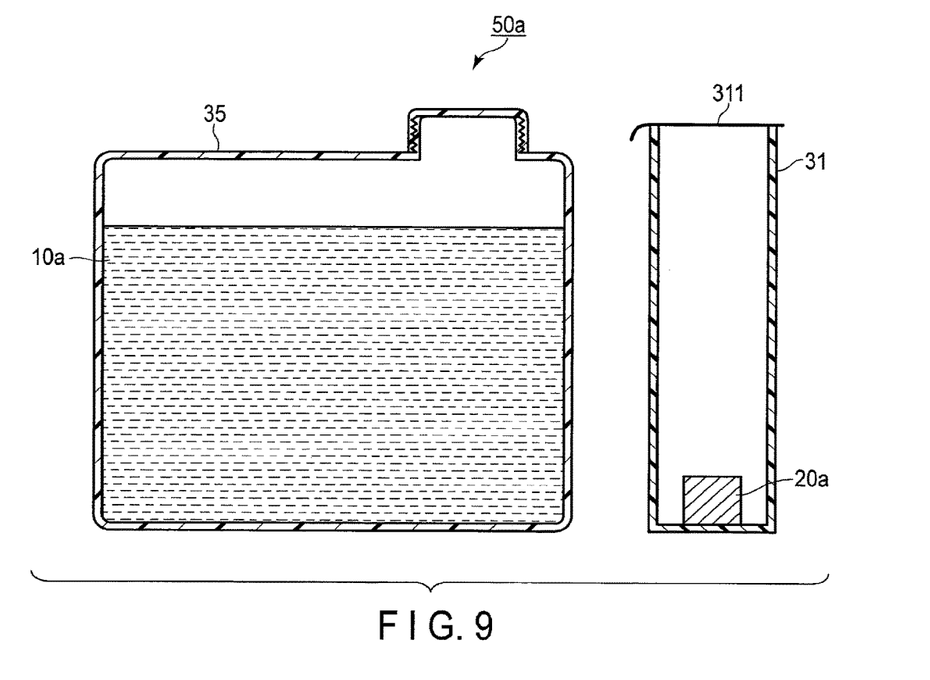
FIG. 9 is a view showing an example of the arrangement of a test reagent according to the second embodiment.

FIG. 9 is a view showing an example of the arrangement of the test reagent 50a. The test reagent 50a includes an aqueous solution 10a such as a buffer solution, and a dry reagent 20a that specifically reacts with the test substance B in the aqueous solution 10a. The test reagent 50a also includes a storage vessel 31 that stores the dry reagent 20a, and a container 35 that stores the aqueous solution 10a to be dispensed into the storage vessel 31 by the specimen measuring apparatus 90a.

The dry reagent 20a is formed from a reagent component 21a and a holding membrane 22. Note that the structure of the dry reagent 20a is similar to the structure of the dry reagent 20 as shown in FIG. 3. The reagent component 21a is in a dry state and specifically reacts with the test substance B in the aqueous solution 10a. The reagent component 21a is formed from a reactant that specifically reacts with the test substance B in the aqueous solution 10a and fine particles on which the reactant is immobilized. The holding membrane 22 has a sheet shape, and the reagent component 21a in the dry state whose dry weight is a predetermined weight dispersed and held by the holding membrane 22.

The opening portion of the storage vessel 31 is sealed by a removable sealing member 311. The dry reagent 20a is hermetically preserved in the storage vessel 31 in the dry state. The container 35 stores the aqueous solution 10a in an amount dispensable to a plurality of storage vessels 31 by the specimen measuring apparatus 90a.

As described above, the reagent component 21a in the dry state is held by the holding membrane 22, and the dry reagent 20a is preserved in the dry state. This makes it possible to prevent the reagent component 21a from deteriorating and preserve it for a long time. In addition, when the reagent component 21a is dispersed and held by the holding membrane 22, the holding membrane 22 disperses in the aqueous solution 10a, and the reagent component 21a is dissolved from the dispersed holding membrane 22. It is therefore possible to prevent the reagent component 21a from remaining undissolved and coagulating and easily diffuse it in the aqueous solution 10a.

The specimen measuring apparatus 90a will be described next.

The specimen measuring apparatus 90a shown in FIG. 8 includes a dispensing unit 70. The dispensing unit 70 dispenses the aqueous solution 10a stored in the container 35 in the test reagent 50a to the storage vessel 31. The dispensing unit 70 also dispenses the aqueous solution 10a into the storage vessel 31, thereby dispensing the aqueous solution 10a containing the reagent component 21a of the dry reagent 20a diffused in the storage vessel 31. The dispensing unit 70 also dispenses a sample.

The specimen measuring apparatus 90a also includes analyzing circuitry 80a that analyzes a reaction state of a measurement solution formed from the sample and the aqueous solution 10a containing the reagent component 21a dispensed by the dispensing unit 70, and display unit 85 that visualizes the analyzing result based on output data from the analyzing circuitry 80a. The specimen measuring apparatus 90a also includes a controller 86a that is a processor functioning as the main unit of the specimen measuring apparatus 90a.

Figure 10:
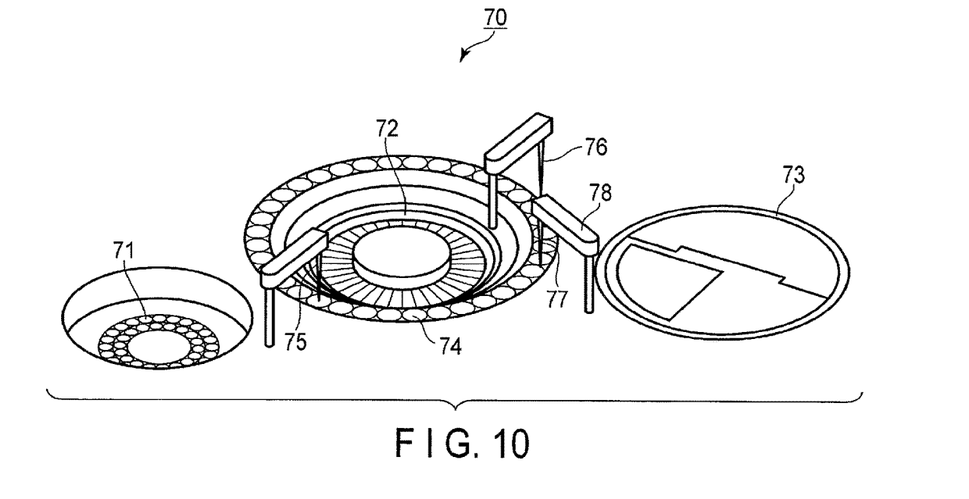
FIG. 10 is a view showing the arrangement of a dispensing unit according to the second embodiment.

FIG. 10 is a view showing the arrangement of the dispensing unit 70. The dispensing unit 70 includes a sample container 71 that stores a sample, and a first reagent storage 72 that stores the container 35. The dispensing unit 70 also includes a second reagent storage 73 that stores the storage vessel 31. The dispensing unit 70 also includes a plurality of reaction vessels 74 arranged to be rotatable. The dispensing unit 70 further includes a sample dispensing probe 75 that performs dispensing of sucking up the sample in the sample container 71 and discharging the sucked sample to the reaction vessels 74.

The dispensing unit 70 also includes a first reagent dispensing probe 76 that performs dispensing of sucking up the aqueous solution 10a in the container 35 stored in the first reagent storage 72 and discharging the sucked aqueous solution 10a to the storage vessel 31 stored in the second reagent storage 73. The dispensing unit 70 also includes a second reagent dispensing probe 77 that performs dispensing of sucking up the aqueous solution 10a in which the reagent component 21a is diffused in the storage vessel 31 upon dispensing of the first reagent dispensing probe 76 and discharging the sucked aqueous solution 10a to the reaction vessels 74. The dispensing unit 70 further includes a level detector 78 that detects the liquid level of the aqueous solution 10a based on the contact between the second reagent dispensing probe 77 and the aqueous solution 10a in the storage vessel 31.

The analyzing circuitry 80a shown in FIG. 8 includes an irradiation device 81a that irradiates the reaction vessel 74 of the dispensing unit 70 with light. The analyzing circuitry 80a also includes a detector 82a that detects the light emitted by the irradiation device 81a and transmitted through the reaction vessel 74. The analyzing circuitry 80a also includes a processor functioning as a data processing circuit 83a that calculates, for example, the concentration of the test substance B contained in the sample based on the light detected by the detector 82a.

An example of the operation of the specimen measuring system 100a will be described below with reference to FIGS. 8 to 10. In the test reagent 50a to be described below, the reactant of the reagent component 21a that forms the dry reagent 20a is an antibody that combines with the test substance B serving as an antigen, and the fine particles are, for example, latex particles. Note that the fine particles may be gold colloid particles.

First, the operator removes the lid from the container 35 of the test reagent 50a, and stores the container 35 without the lid in the first reagent storage 72 of the dispensing unit 70. The operator also removes the sealing member 311 from each of, for example, three storage vessels 31 as many as the number of samples that undergo the test of the test substance B, and stores the storage vessels 31 without the sealing member 311 in the second reagent storage 73. When the specimen measuring apparatus 90a starts measurement, the first reagent dispensing probe 76 sucks up the aqueous solution 10a in the container 35 in the first reagent storage 72 and dispenses a preset amount of aqueous solution 10a into the storage vessel 31 in the second reagent storage 73. This dispensing operation is repeated for the three storage vessels 31 stored in the second reagent storage 73. In each storage vessel 31, when the aqueous solution 10a is dispensed, the holding membrane 22 of the dry reagent 20a disperses in the aqueous solution 10a, and the reagent component 21a is diffused in the aqueous solution 10a. When a predetermined time elapses, the dispersed holding membrane 22 precipitates in the state in which the reagent component 21a is diffused in the aqueous solution 10a.

As described above, when the aqueous solution 10a is dispensed into the storage vessel 31, the holding membrane 22 disperses in the aqueous solution 10a, and the reagent component 21a is dissolved from the dispersed holding membrane 22. It is therefore possible to prevent the reagent component 21a from remaining undissolved and coagulating and easily diffuse it in the aqueous solution 10a.

Note that the aqueous solution 10a in the container 35 stored in the first reagent storage 72 and the reagent component 21a held in the dry state by the holding membrane 22 in the storage vessel 31 stored in the second reagent storage 73 do not deteriorate at room temperature during the test. In addition, the aqueous solution 10a can be dispensed to the storage vessels 31 in a number necessary for the test of the test substance B, and the reagent component 21a in the aqueous solution 10a in the storage vessels 31 in which the aqueous solution 10a is dispensed does not deteriorate at room temperature during the test. Since the first reagent storage 72 and the second reagent storage 73 need not be provided with a cooling mechanism, the specimen measuring apparatus 90a can be made simple and compact. It is also possible to reduce power consumption.

The sample dispensing probe 75 sucks up the sample in the three sample containers 71 and dispenses a preset amount of sample to three reaction vessels 74. After the elapse of a predetermined time or more from the dispensing of the aqueous solution 10a, the second reagent dispensing probe 77 stops at a position lowered by a predetermined distance from a position at which the liquid level of the aqueous solution 10a in the nth (n is a positive integer: 1≤n≤3) storage vessel 31 out of the three storage vessels is detected by the level detector 78. The stop position is a position at which a preset dispensing amount of aqueous solution 10a containing the reagent component 21a diffused in the storage vessel 31 can be sucked, and is located above the holding membrane 22 that has precipitated. The aqueous solution 10a is sucked up at the stop position, and the sucked aqueous solution 10a is discharged into the nth reaction vessel 74 in which the sample is dispensed.

In the measurement solution formed from the sample and the aqueous solution 10a containing the reagent component 21a in each reaction vessel 74, coagulation occurs due to the reaction between the test substance B contained in the sample and the reagent component 21a contained in the aqueous solution 10a. The analyzing circuitry 80a detects a light transmitted through the turbid measurement solution due to the coagulation. The data processing circuit 83a of the analyzing circuitry 80a calculates the concentration of the test substance B contained in the sample based on the detected light. The display unit 85 displays the concentration of the test substance B calculated by the analyzing circuitry 80a.

Note that the change in the turbidity caused by the coagulation may be analyzed by detecting a scattered light at a predetermined angle in the measurement solution in the reaction vessel 74.

As described above, after the elapse of a predetermined time or more from the dispensing of the aqueous solution 10a into the storage vessel 31, the dispersed holding membrane 22 precipitates in the state in which the reagent component 21a is diffused in the aqueous solution 10a. Therefore the dispensing unit 70 can dispense, to the reaction vessel 74, the aqueous solution 10a in which the reagent component 21a other than the holding membrane 22 is diffused. This makes it possible to quickly test the test substance B contained in a plurality of samples without a burden on the operator.

Note that the second embodiment is not limited to the above-described embodiment. If the test substance is a test substance C, a dry reagent 20b in which a reagent component 21b in a dry state is held by the holding membrane 22 is used. Note that the structure of the dry reagent 20b is similar to the structure of the dry reagent 20 as shown in FIG. 3. The reagent component 21b is formed from, for example, an antibody that reacts with the test substance C as an antigen labeled by a chemiluminescent substance such as luminol and fine particles on which the antibody is immobilized. In addition, a reaction vessel 74a formed by immobilizing, in the reaction vessel 74, an antibody that combines with the test substance C in an aqueous solution 10b is used. After the elapse of a predetermined time or more from the dispensing of the aqueous solution 10b to the storage vessel 31 storing the dry reagent 20b, the aqueous solution 10b containing the sample and the reagent component 21b is dispensed into the reaction vessel 74a. Next, after the aqueous solution 10b is drained from the reaction vessel 74a, the interior of the reaction vessel 74a may be irradiated with excitation light, thereby detecting fluorescence emitted by the reagent component 21b combined, via the test substance C, with the antibody immobilized in the reaction vessel 74a and measuring the test substance C.

If the test substance is a test substance D, a dry reagent 20c in which a reagent component 21c in a dry state is held by the holding membrane 22 is used. Note that the structure of the dry reagent 20c is similar to the structure of the dry reagent 20 as shown in FIG. 3. The reagent component 21c contains a reactant that reacts with the test substance D in an aqueous solution 10c and generates a substance that absorbs light in a predetermined wavelength region. After the elapse of a predetermined time or more from the dispensing of the aqueous solution 10c to the storage vessel 31 storing the dry reagent 20c, the aqueous solution 10c containing the sample and the reagent component 21c is dispensed into the reaction vessel 74. Next, the test substance D may be measured by detecting light in a predetermined wavelength region which passes through the measurement solution formed from the aqueous solution 10c containing the sample and the reagent component 21c in the reaction vessel 74.

According to the above-described second embodiment, the dry reagent 20a in which the reagent component 21a in the dry state is held by the holding membrane 22 is preserved in the dry state. This makes it possible to prevent the reagent component 21a from deteriorating and preserve it for a long time. In addition, when the aqueous solution 10a is dispensed to the storage vessel 31 that stores the dry reagent 20a, the holding membrane 22 disperses in the aqueous solution 10a, and the reagent component 21a can easily be diffused in the aqueous solution 10a. After the elapse of a predetermined time or more from the dispensing of the aqueous solution 10a to the storage vessel 31, the aqueous solution 10a in which reagent component 21a other than the holding membrane 22 is diffused is dispensed to the reaction vessel 74. This makes it possible to easily test the test substance B contained in a plurality of samples without a burden on the operator.

The term "processor" used in the above explanation means, for example, circuitry such as a CPU (Central Processing Unit), a GPU (Graphics Processing Unit), an ASIC (Application Specific Integrated Circuit), or a programmable logic device (for example, an SPLD (Simple Programmable Logic Device), a CPLD (Complex Programmable Logic Device), or an FPGA (Field Programmable Gate Array)). The processor implements a function by loading and executing a program saved in storage circuitry. Note that each processor of the embodiments is not necessarily formed as single circuitry. A plurality of independent circuitry may be combined to form one processor and implement the function. The data processing circuit 83 and the controller 86 shown in FIG. 1 may be implemented by one processor. The data processing circuit 83a and the controller 86a shown in FIG. 8 may be implemented by one processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A test reagent kit comprising:
a test reagent comprising a reactant and a sheet-shaped member, wherein the reactant is in a dry state and specifically reacts with a test substance, and the sheet-shaped member holds the reactant, disperses in a solvent solution, and is a fibrous substance that is not concerned in the reaction between the test substance and the reactant;
a container comprising a storage vessel and a nozzle, the storage vessel being configured to store the solvent solution and in which the test reagent is to be put; and
a filter stored in the container between the storage vessel and the nozzle, and configured to separate the dispersed sheet-shaped member dispersed in the solvent solution from a solution mixture of the test reagent and the test substance put in the solvent solution,
wherein the nozzle is configured to externally pour a measurement solution in which the sheet-shaped member is separated from the solution mixture by the filter.

2. The test reagent kit according to claim 1, wherein the fibrous substance that is not concerned in the reaction between the test substance and the reactant is one of a substance containing cellulose and a water soluble resin.

3. The test reagent kit according to claim 1, wherein the reactant comprises an antibody that combines with the test substance serving as an antigen.

4. The test reagent kit according to claim 1, wherein the reactant is immobilized on a fine particle, and the fine particle is held by the sheet-shaped member.

5. The test reagent kit according to claim 4, wherein the fine particle comprises one of a magnetic particle, a latex particle, and a gold colloid particle.

6. The test reagent kit according to claim 1, wherein the reactant is labeled by a chemiluminescent substance.

7. The test reagent kit according to claim 1, wherein the reactant generates a substance that absorbs light in a predetermined wavelength region by the reaction with the test substance.

8. The test reagent kit according to claim 1, wherein the storage vessel is made of a soft material and configured to be pressed to expel measurement solution from the nozzle.

9. A specimen measuring system that measures the test substance using the measurement solution flowing out from the nozzle included in the test reagent kit of claim 1.

10. The specimen measuring system according to claim 9, comprising a reaction chamber in which a solution is injected,
wherein the test reagent is put in the solvent solution,
the sheet-shaped member dispersed in the solvent solution is separated by the filter, and
the nozzle pours the measurement solution.

11. The specimen measuring system according to claim 10, wherein the reactant comprises an antibody that is immobilized on a magnetic particle and combines with the test substance serving as an antigen, and
an optical waveguide is provided as one surface of the reaction chamber.

12. The specimen measuring system according to claim 11, further comprising:
magnetic field applying circuitry configured to apply a magnetic field to the reaction chamber; and
analyzing circuitry configured to analyze a change of a physical value between light propagated through the optical waveguide before the magnetic field is applied and light propagated through the optical waveguide after the magnetic field is applied.

13. The specimen measuring system according to claim 9, further comprising:
a reagent storage configured to hold a vessel storing the test reagent;
a first reagent dispensing probe configured to dispense the solvent solution into the vessel; and
a second reagent dispensing probe configured to dispense the solution, into a reaction vessel, from the vessel in which the solvent solution has been dispensed.

* * * * *